(12) United States Patent
Dumas (10) Patent No.: US 8,152,519 B1
(45) Date of Patent: Apr. 10, 2012

(54) ORTHODONTIC CONNECTOR ASSEMBLY AND A METHOD FOR TREATING TEETH

(76) Inventor: John Joseph Dumas, Bloomfield Hills, MI (US)

( * ) Notice: Subject to any disclaimer, the term of this patent is extended or adjusted under 35 U.S.C. 154(b) by 462 days.

(21) Appl. No.: 11/724,140

(22) Filed: Mar. 14, 2007

(51) Int. Cl.
*A61C 3/00* (2006.01)

(52) U.S. Cl. .............................. 433/8; 433/10

(58) Field of Classification Search ............... 433/8–16, 433/24
See application file for complete search history.

(56) References Cited

U.S. PATENT DOCUMENTS

| | | | |
|---|---|---|---|
| 3,721,005 A * | 3/1973 | Cohen | 433/16 |
| 3,959,880 A | 6/1976 | Andrews | |
| 3,975,824 A | 8/1976 | Lee | |
| 4,180,912 A | 1/1980 | Kesling | |
| 4,427,381 A * | 1/1984 | Hall | 433/14 |
| 4,496,317 A * | 1/1985 | Hulsey | 433/10 |
| 4,496,318 A | 1/1985 | Connelly, Jr. | |
| 4,525,143 A | 6/1985 | Adams | |
| 4,585,413 A | 4/1986 | Wool | |
| 4,957,438 A | 9/1990 | Bax | |
| 5,356,288 A * | 10/1994 | Cohen | 433/8 |
| 5,580,243 A | 12/1996 | Bloore | |
| 6,726,474 B2 | 4/2004 | Spencer | |
| 7,722,354 B1 | 5/2010 | Dumas | |
| 2002/0058227 A1 | 5/2002 | Townsend-hansen | |
| 2004/0157184 A1 | 8/2004 | Reising | |
| 2005/0255422 A1 | 11/2005 | Cordato | |
| 2005/0277082 A1 | 12/2005 | Christoff | |
| 2006/0199137 A1 | 9/2006 | Abels et al. | |
| 2006/0269891 A1 | 11/2006 | Miqui | |

* cited by examiner

*Primary Examiner* — Todd Manahan
*Assistant Examiner* — Yogesh Patel (57) ABSTRACT

An orthodontic connector assembly 10 including a plurality of substantially identical connecting members, such as members 12, 14 which include a movable but biased portion 20 which is adapted to selectively and removably receive a pocket portion 44 which is deployed on at least one bracket, such as bracket 40. In an alternative embodiment, the members, such as member 12, 14 each include a ridge, such as ridge 212, which is selectively, removably, and frictionally placed within slot 236.

4 Claims, 9 Drawing Sheets

ORTHODONTIC CONNECTOR ASSEMBLY AND A METHOD FOR TREATING TEETH

GENERAL BACKGROUND

1. Field of the Invention

The present invention generally relates to an orthodontic connector assembly and to a method for treating teeth and more particularly, to an assembly which allows orthodontic brackets, even a plurality of dissimilar brackets, to be selectively and removably coupled to teeth in a manner which forms a method for effectively and therapeutically treating teeth.

2. Background of the Invention

Orthodontic brackets, often referred to as "braces", are devices which are normally and selectively affixed to the teeth of an individual, by the use of cement or another type of bonding agent, and are adapted to selectively receive a wire which is formed and deployed in the brackets (e.g., in the mouth of a patient) in order to provide therapeutic force or pressure on the patient's teeth. The combination of the brackets and the wire are often sometimes collectively referred to as a "retaining system" or an "orthodontic retaining system".

While such prior and currently utilized retaining systems do allow therapeutic pressure to be applied to a patient's teeth, they suffer from some drawbacks.

By way of example and without limitation, as the therapy is applied to the patient (i.e., over time) modifications may need to be made to the brackets or different brackets may be optimally needed. This "bracket modification" or "replacement" is complicated and time consuming because the currently utilized brackets must be forcibly removed from the patient's teeth (e.g., removed from the cement or adhering agent), the teeth must be cleaned and "re-prepped" (an etching agent and a new application of an adhering agent must be deployed on the teeth), and the new or modified brackets must be deployed on the newly prepped teeth. The process is uncomfortable to the patient and is relatively costly due to the need for additional etching and adhesive material and the time needed to achieve the change or modification. Moreover, sometimes the deployed brackets become broken or are in need of repair and must be removed from the patient's teeth to become serviced, thereby requiring the same sort of afore-described process and relatively the same sort of cost and discomfort.

Further, it may be therapeutically desirable to deploy different sorts or types of brackets upon the teeth of a patient within a relatively short amount of time due to the needs of the patient and such "rapid bracket deployment" undesirably and greatly increases the cost and discomfort to the patient. Further, different sorts of brackets may be used on a patient, within a certain time, just in order for a orthodontist to evaluate the efficacy of these deployed brackets on a certain patient and discover the bracket type which may provide optimal therapy on a particular patient (i.e., each patient may experience different amounts and types of therapy with a certain bracket). Non-limiting examples of orthodontic brackets are found within United States Patent Application Publication Numbers US2005/0255422 A1, US2002/0058227 A1, and US2004/0157184 A1 which are each fully and completely incorporated herein by reference, word for word and paragraph for paragraph.

There is therefore a need for a new and improved connector assembly which allows brackets and orthodontic retaining systems to be easily, quickly, and cost effectively deployed upon the teeth of a patient and it is one non-limiting object of the present invention to provide such an improved connector system.

SUMMARY OF THE INVENTION

It is a first non-limiting object of the present invention to provide a new and novel orthodontic connector assembly which overcome some or all of the previously delineated disadvantages of prior connector systems.

It is a second non-limiting object of the present invention to provide a new and improved methodology for treating teeth which overcome some or all of the previously delineated disadvantages of prior and current strategies and methodologies.

According to a first non-limiting aspect of the present invention, an orthodontic connector assembly is provided and includes a plurality of substantially identical connector members which are each selectively and respectively adhered to unique teeth and each of which include a substantially identical connector portion, wherein each of the substantially identical connector portions cooperatively and removably receive a bracket.

According to a second non-limiting aspect of the present invention, an orthodontic connector assembly is provided and includes the combination of a plurality of substantially identical connector members which each include a first smooth surface which is respectively and selectively adhered to unique teeth and each of which further respectively include a second opposed surface which includes a ridge and wherein each of the ridges are substantially identical and have a certain first shape; and a plurality of brackets which include a first back surface having a slot having a complementary shape to each of said ridges and where each of said slots are adapted to receive a unique one of each of the ridges and wherein each of the plurality of brackets include dissimilar front wire reception portions.

According to a third non-limiting embodiment of the invention, a bracket is provided and includes a back surface which includes a slot and a front surface which includes a plurality of protuberances which cooperatively form a slot and a member which is pivotally coupled to the front surface and which includes a nub portion which extends from said front surface.

According to a fourth non-limiting aspect of the present invention, a method for therapeutically treating teeth is provided. Particularly, the method includes the steps of providing a plurality of substantially identical connector members, wherein each of the substantially identical connector members has a certain first shape which includes a central ridge; respectively fixing each of the plurality of substantially identical connector members onto a unique tooth in a manner which allows each of the central ridge to protrude from a respectively unique tooth; providing a plurality of dissimilar brackets, each of the brackets including a slot; causing the respective slot of each of said plurality of dissimilar brackets to be connected to a unique one of the central ridges.

These and other features, aspects, and advantages of the present invention will become apparent by a reading of the detailed description of the preferred embodiment of the invention, including the subjoined claims and by reference to the drawings.

DETAILED DESCRIPTION OF THE PREFERRED EMBODIMENT OF THE INVENTION

Referring now to FIGS. 1, 2, 3, and 6, there is shown an orthodontic connector assembly 10 which is made in accordance with the teachings of the preferred embodiment of the invention.

Figure 1:
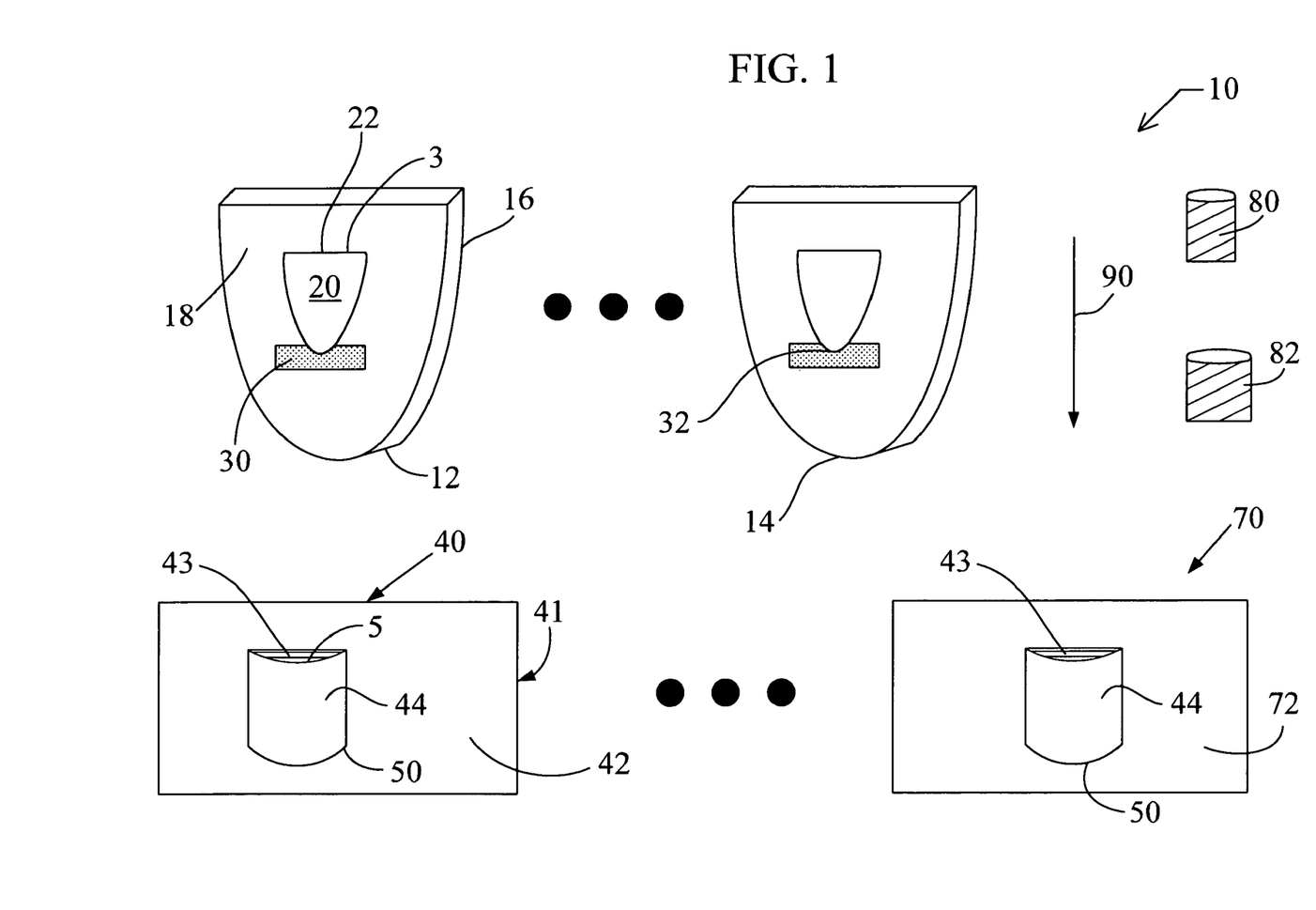
FIG. 1 is a perspective view of a orthodontic connector assembly which is made in accordance with the teachings of the preferred embodiment of the invention.

Particularly, the orthodontic connector assembly 10 includes a plurality of substantially identical connector members, such as members 12, 14, which may be constructed from metal, plastic or another composite material and which includes a first substantially flat back surface 16 and a second substantially flat front surface 18. The connector members, such as members 12, 14, are of a size and a shape which is smaller than the size and shape of a human tooth. Nothing in this description is meant to limit the members 12, 14 to any particular size and shape or to any particular material and, in various alternate embodiments of the invention, many connector members of different sizes and shapes may be provided.

The surface 18 includes a portion 20 which is hingedly coupled (e.g., by a hinge member 3 which is coupled to surface 18 and to member 20) to the surface 18 along the edge 22 and thus normally contacts (i.e., is biased against) surface 18 but may be selectively moved from this first surface contacting position to a second non-contacting position away from surfaces 18 and 16. In one non-limiting embodiment, hinge member 3 may space a spring or other device which allows portion 20 to be selectively and movably coupled to surface 18 but which causes portion 20 to be biased against surface 18. Portion 20 may be of substantially any desired shape. The surface 18 further includes a raised edge portion 30 upon which the far edge 32 of portion 20 overlays (e.g., the term "far edge", in this context, means the part of portion 20 farthest away form edge 22).

The connector assembly 10 further includes at least one bracket 40 having a generally flat back surface 42 upon which a pocket portion 44 is formed. A pocket portion 44 may comprise a generally "c-shape" member which is coupled to the surface 42 and which includes an opening 43 which extends through the entire pocket portion 44 and which lies between surface 42 and inner surface 5 of the portion 44. The at least one bracket 40 may have a front portion 41 of any desired size and shape therapeutic configuration and the pocket portion 44 is adapted to receive the portion 20, of a member 12, after it is raised off of the surface 18 that it normally is biased against by the edge 22 (e.g., the member 20 is selectively received within and extends through opening 43 in a manner which allows surface 41 to cover the portion 44 from view). The pocket portion 44 may be integrally formed with bracket 40 or attached to bracket 40 by adhesive or any other similar type of material.

The front portion 41 may be adapted to receive a wire or any other therapeutic member or element. After the pocket 44 receives the raised portion 20 (e.g., the portion 20 is inserted through opening 43 of the pocket portion 44) it is ensured that the bottom edge 50 of the pocket portion 44 is supported by edge 30 and then the raised portion 20 is allowed to be biased back toward surface 18 by the biasing member 22, thereby fixing the pocket portion 44 against the surface 18 and attaching the bracket 40 to the portion 12, as shown best in FIG. 6. The edge 30 cooperates with the edge 50 to further attach the bracket 40 to the member 12. It should be appreciated that bracket, such as bracket 70, which may be dissimilar to bracket 40, is made to have a substantially identical back surface 72 which is similar to back surface 41 (i.e., each dissimilar bracket is made to have a substantially similar back surface and thereby includes a substantially identical pocket 44). Thus, every bracket to be utilized as part of or in combination with the assembly 10 must, in the most preferred although non-limiting embodiment, include a back portion which is substantially similar to back portions 42, 72 (e.g., having a pocket portion 44) but which may have a respectively unique and therapeutic front portion (i.e., a portion which receives a wire). In this manner, the respective therapeutic front portion (e.g., portion 41) always outwardly extends from the front surface 7 of each tooth (e.g., the surface which is visible, in the manner which is shown, for example, in FIGS. 3 and 6. Thus, a first set of substantially identical brackets (one for each tooth to be treated) may be deployed, such that each bracket is deployed upon a unique tooth 9, 11 within the mouth of a patient (e.g., each of these brackets has a substantially identical front portion 41 and substantially identical back portion 42). A second set of brackets, each having a front portion which is dissimilar to the front portion of the first set of brackets, may replace the first set of brackets, if the need arises. Alternatively, dissimilar brackets (e.g., those having respectively different therapeutic front portions) may be concurrently utilized upon various teeth within the mouth of a patient if the need arises.

The connector assembly 10 may also include a quantity of cement or an adhesive 80 and some etching material or acid 82. In other non-limiting embodiments of the invention, the assembly 10 does not include the adhesive 80 or etching material 82 or any brackets, such as bracket 40.

Figure 2:
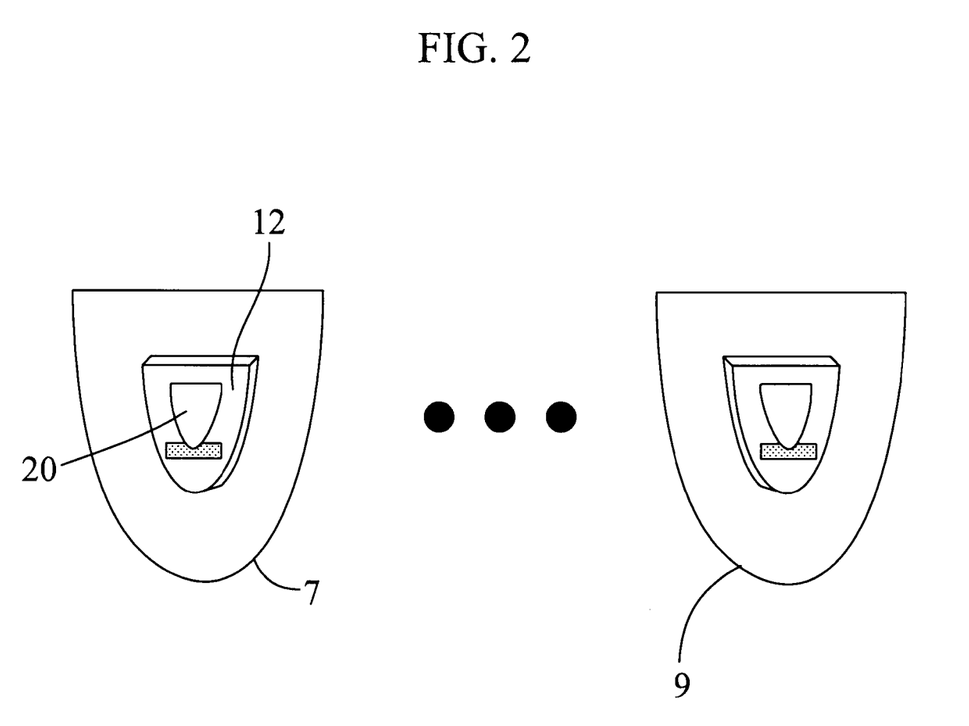
FIG. 2 is a partial front view of a portion of a patient's mouth showing a partial deployment of the orthodontic connector assembly which is shown in FIG. 1, upon certain teeth.
Figure 3:
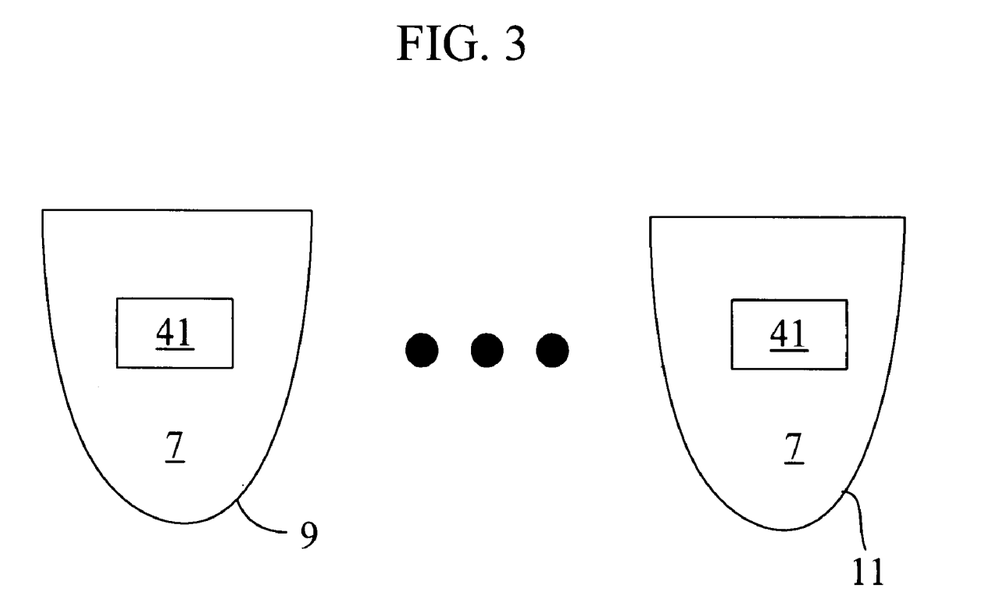
FIG. 3 is a partial front view of a patient's mouth into which the orthodontic connector assembly of the preferred embodiment of the invention is operatively deployed.

As shown best in FIGS. 2 and 3, teeth, such as teeth 7, 9, which are to receive the substantially identical members, such as members 12, 14, are first etched with the material 82 and then the attaching material 80 is applied to the previously etched teeth and then the respective surface 16 of each respective member 12, 14 is placed onto a respectively unique tooth 7, 9 (i.e., onto the previously deployed material 80), until all of teeth 7,9 which are to be therapeutically manipulated have received a unique member 12.

Brackets, such as bracket 40 may be easily applied and removed from each of the deployed members 12 (e.g., a bracket, such as bracket 40 is removed simply by moving the portion 20 away from the surface 18 and sliding the pocket 44 downwards in the direction 90). In this manner, brackets, such as bracket 40, may be easily applied and removed from teeth.

Thus, it should be appreciated that this forgoing invention describes a system and a technique by which dissimilar brackets are made to have a common back portion 42, 72 which is adapted to selectively and removably receive a standardized member 12, 14 which has been placed upon teeth. In this manner, dissimilar brackets (e.g., those with different therapeutic or "wire receiving" frontal portions 41) may be easily placed upon and removed from teeth (e.g., front portion 20). It should also be appreciated that the shape of portions 20 and pocket 44 may change as desired and that nothing in this description is meant to limit the shape of portion 20 in any manner.

Figure 4:
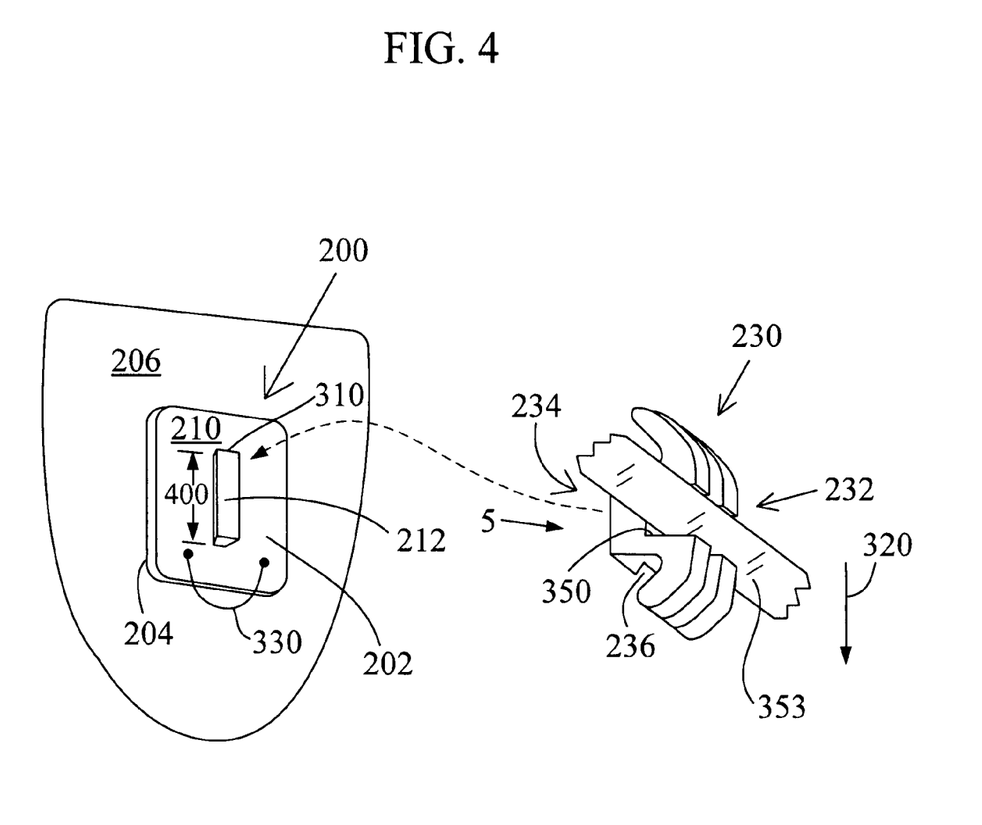
FIG. 4 is a perspective view of an orthodonic connector assembly which is made in accordance with the teachings of an alternate embodiment of the invention in unassembled combination with an orthodonic bracket made according to the invention.
Figure 5:
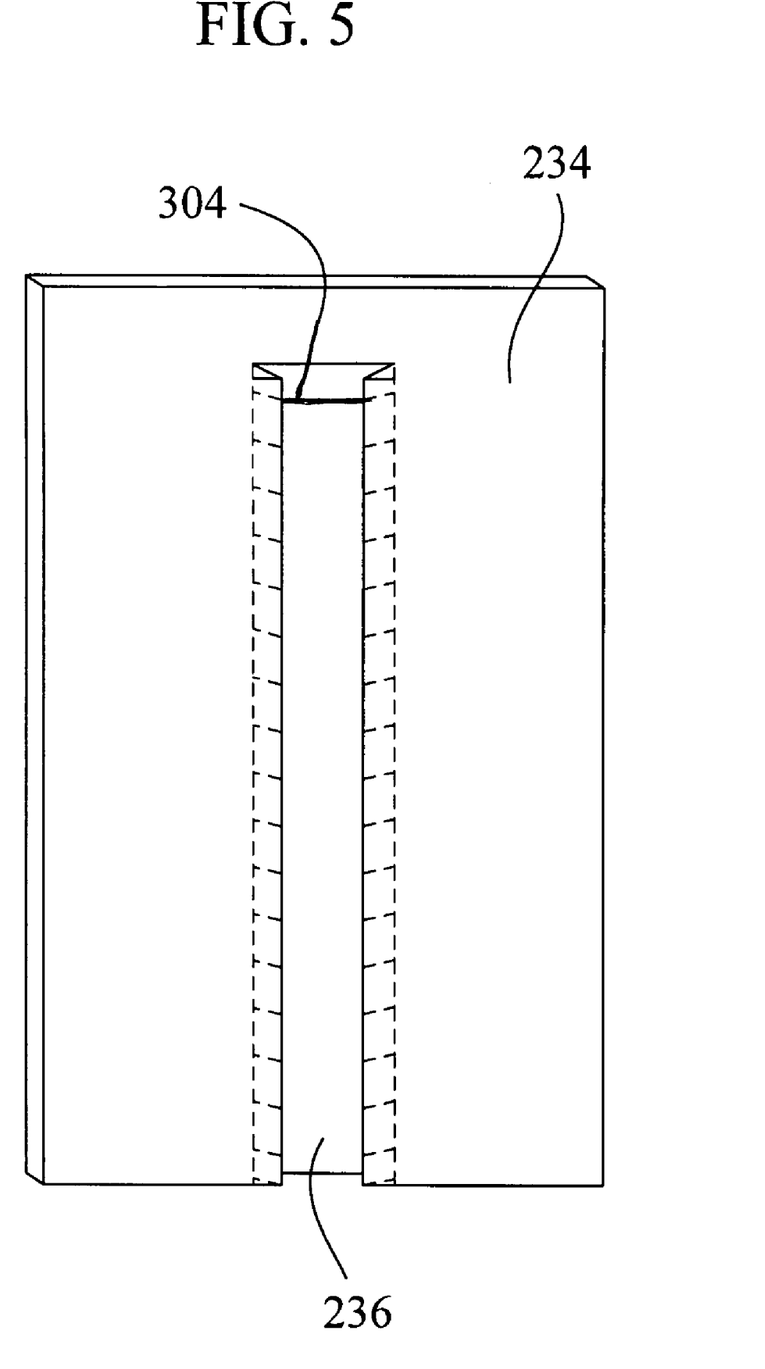
FIG. 5 is a back view of the orthodonic bracket taken in the direction of arrow 5 of FIG. 4.
Figure 6:
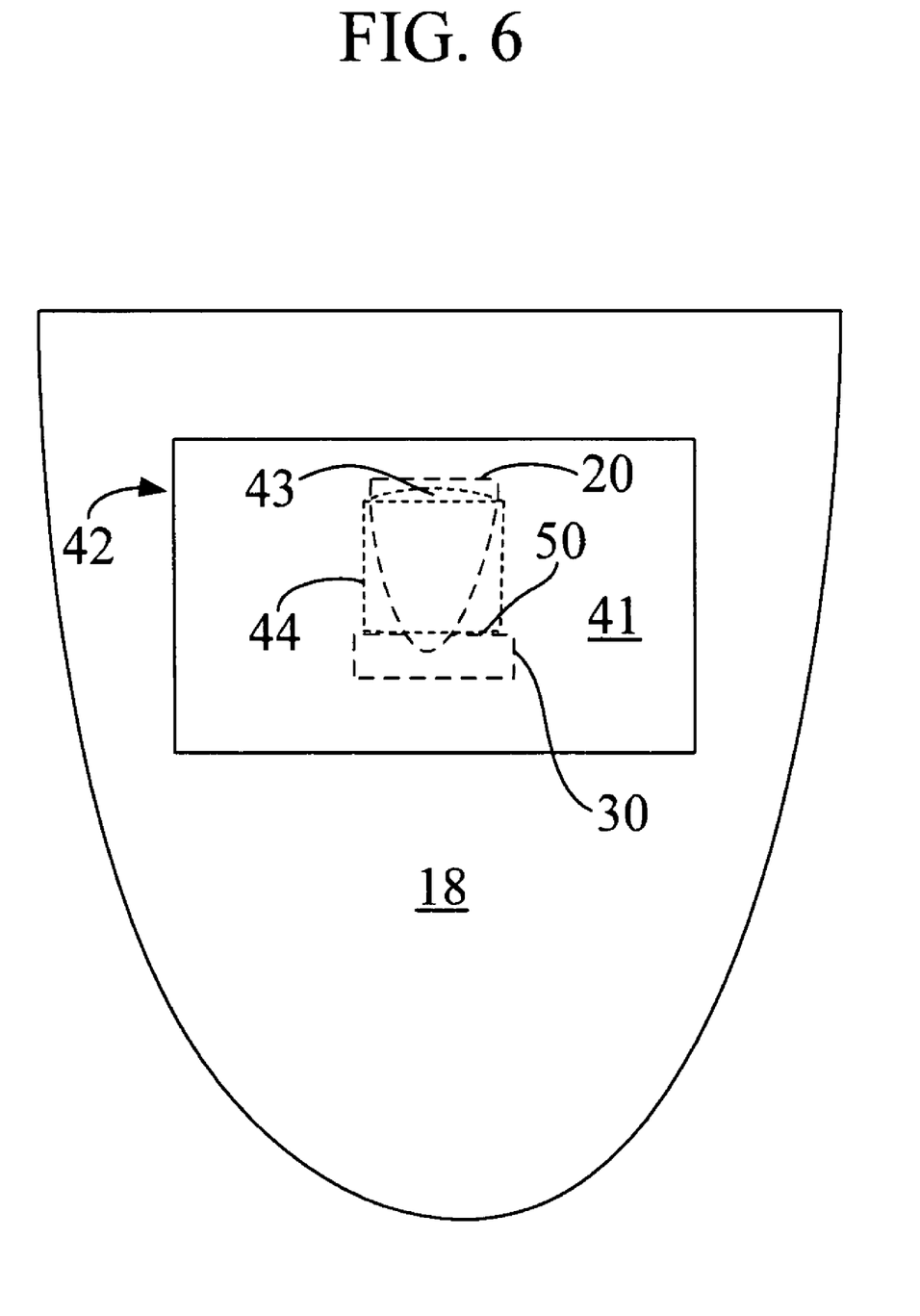
FIG. 6 is a front view of one of the teeth which are shown in FIG. 3 showing, in phantom, the manner in which a portion of the connector assembly, shown in FIG. 1, is attached to the tooth.

Referring now to FIGS. 4-5, there is shown a connector member 200 which is made in accordance with the teachings of an alternate embodiment of the invention and which includes a substantially flat base portion 202 having a flat back surface 204 which is adapted to be selectively attached to a tooth, such as tooth 206, such as by use of attaching material 80. The member 202 has a substantially flat front surface 210 having a protruding central ridge portion 212 which protrudes away from surfaces 210 and 204, and from tooth 206 when the member 202 is selectively attached to the tooth 206 (e.g., by use of cement/glue).

The bracket, such as bracket 230, has a therapeutic front portion 232, which may be configured as desired and which is selectively adapted to receive wire, such as wire 353, and a back portion 234 having a depression or slot 236 which is adapted to selectively and removably and fixedly receive the member 212 (e.g., the slot 236 selectively "slides onto" and frictionally engages and receives member 212), thereby allowing the back surface 234 to be slidably, frictionally, selectively, and removably fixed onto member 212. In this manner, each tooth, such as tooth 206, may receive a connector member 200 and have the connector member 200 selectively adhered to it, thereby allowing a bracket, such as bracket 230, to be connected to the member 200 and selectively removed from it (e.g., by having the member 230 selectively and forcibly "slide away" from the ridge 212). The ridge 212 may be of any shape including a columnar shape and the shape of ridge 212 is "complimentary" to the shape of the slot 236 (e.g., the term "complimentary" means a ridge 212 is adapted to be selectively, slidably, removably and frictionally received within a slot 236 and to be later selectively and frictionally removed from the slot 236).

In yet another non-limiting embodiment of the invention, the slot 236 may include at least one ridge 304, which may be placed within and/or formed within the slot 236 and which is adapted to selectively engage edge 310 of ridge member 212 to prevent movement of deployed bracket 230 in the direction of arrow 320. In this manner, the deployed bracket, such as bracket 230 may be adjusted to occupy a certain position along length 400 of a member 212 but will never move out of engagement with member 212 while traveling along direction 320. Additionally, a relatively thin wire strap, such as strap 330, may be deployed upon surface 210 and adapted to be placed around the interior slot portion 350 of the bracket 230 after slot 236 receives ridge 212, thereby further securing the bracket 230 to the member 210. Therapeutic wire 353 may, of course, later be placed within slot 350 (i.e., after strap 330 is made to selectively occupy the slot 350).

Figure 7:
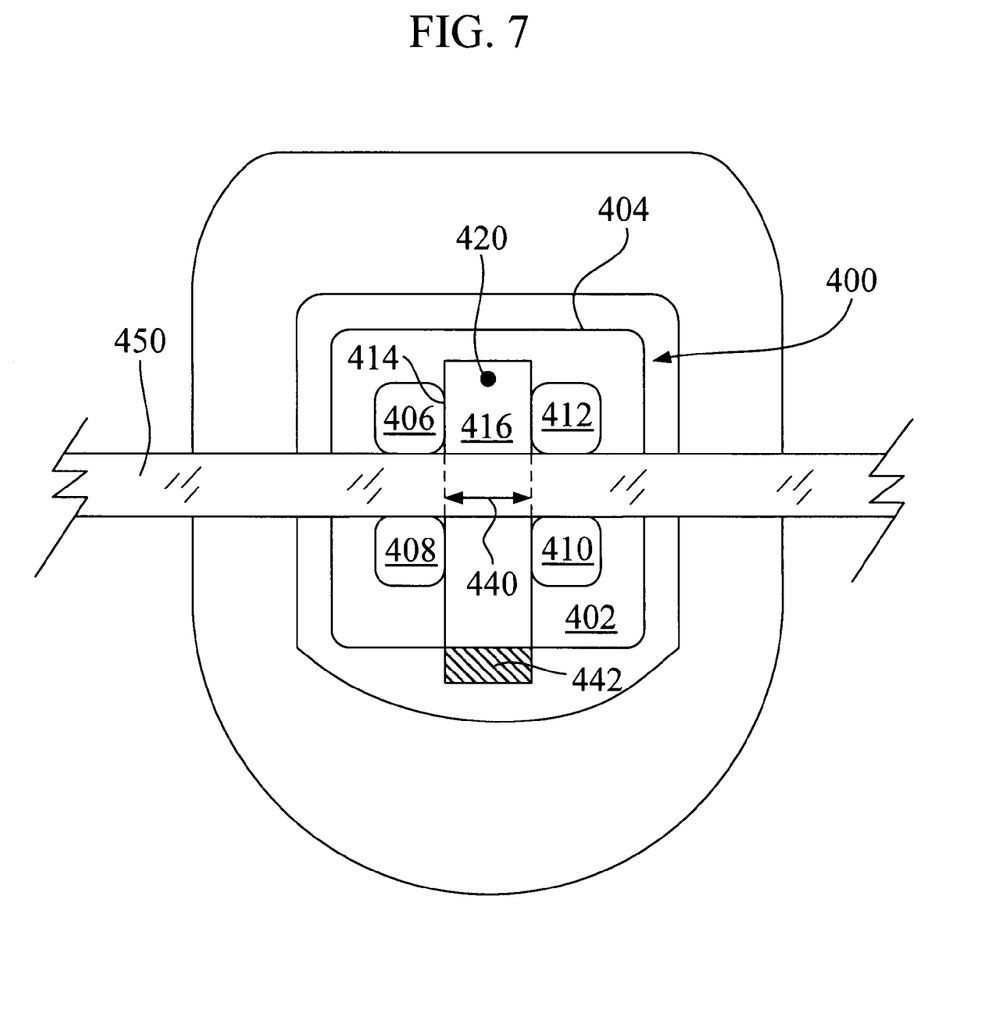
FIG. 7 is a front view of a bracket which is made in accordance with the teachings of the present invention.
Figures 8, 9:
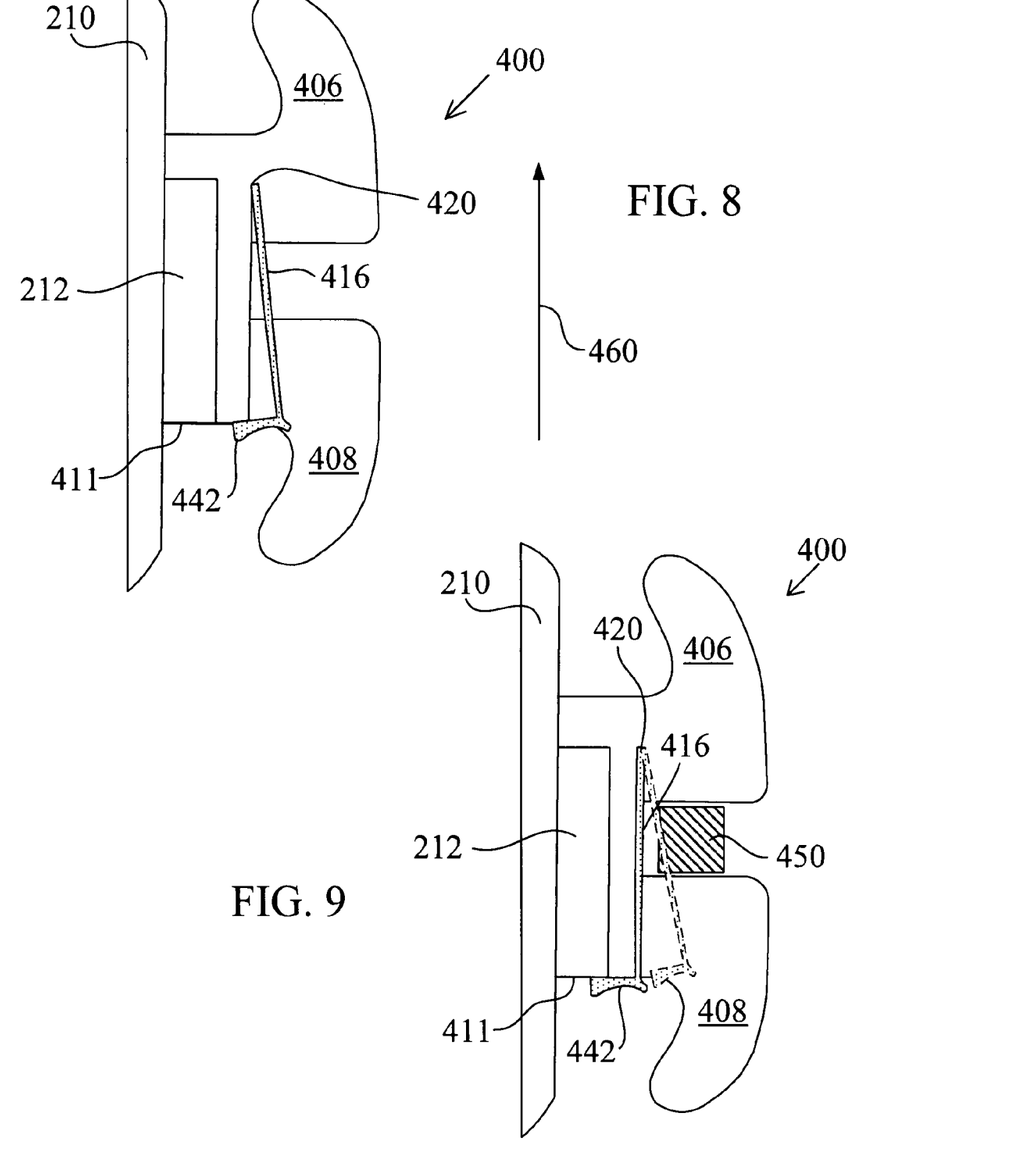
FIG. 8 is a partial side sectional view of the bracket which is shown in FIG. 7 selectively deployed upon a connector member which is made in accordance with the teachings of an alternate embodiment of the invention, before therapeutic wire is received.
FIG. 9 is a view which is similar to that which is shown in FIG. 8, but including a therapeutic wire.

Referring now to FIGS. 7, 8 and 9, there is shown a bracket 400 which is made in accordance with the teachings of the invention. Particularly, bracket 400 includes a front surface 402 and a back surface 404 which may be substantially similar to back surface or portion 234 which is shown in FIG. 5.

Front surface 402 includes four substantially similar protuberances 406, 408, 410, and 412 which cooperatively form a channel 414 in which member 416 resides. Particularly, member 416 is pivotally coupled to surface 402 by attachment pin 420 or a tack weld and has a width 440 which is substantially equal to the width of the channel 414 and member 416 has a nub or protuberance portion 442 which extends off of and away from the surface 402 and away from pin 420. In one non-limiting embodiment of the invention, the nub portion 442 "curls" or projects away from surface 402 and toward surface 404.

In operation, the bracket 400 may be attached to the member 212 in the manner which has been previously delineated (e.g., as the back surface 404 is placed onto the ridge member 212, the nub 442 is made to forcibly pivot away from the surface 402 until the surface 404 is secured onto the member 212 at which time the nub 442 engages the surface 411 of the member 212 onto which it is deployed). Thus, in this embodiment, the bracket 400 is given additional "stability" (e.g. has a reduced likelihood of movement off of member 212) due to the fact that nub 442 frictionally engages the surface 411 of the member 212, when the bracket 400 is attached to member 210, thereby preventing or substantially reducing the likelihood of movement of the bracket 400 from surface 210. Further, wire 450 may be placed between the protuberances 406, 408, 410 and 412, thereby further securing the bracket 400 to the surface 210 by preventing disengagement of member 416. When it is desired to remove the bracket 400 from the member 212, the wire 450 is removed, the member 416 is pivoted away from the surface 402 (i.e., shown in phantom in FIG. 9), thereby causing nub 442 to be in a "non-contact" relationship with 411 portion of 212 and then the back surface of the bracket 400 is "slid away" from contact with ridge 212 in the direction of arrow 460.

Figures 10, 11:
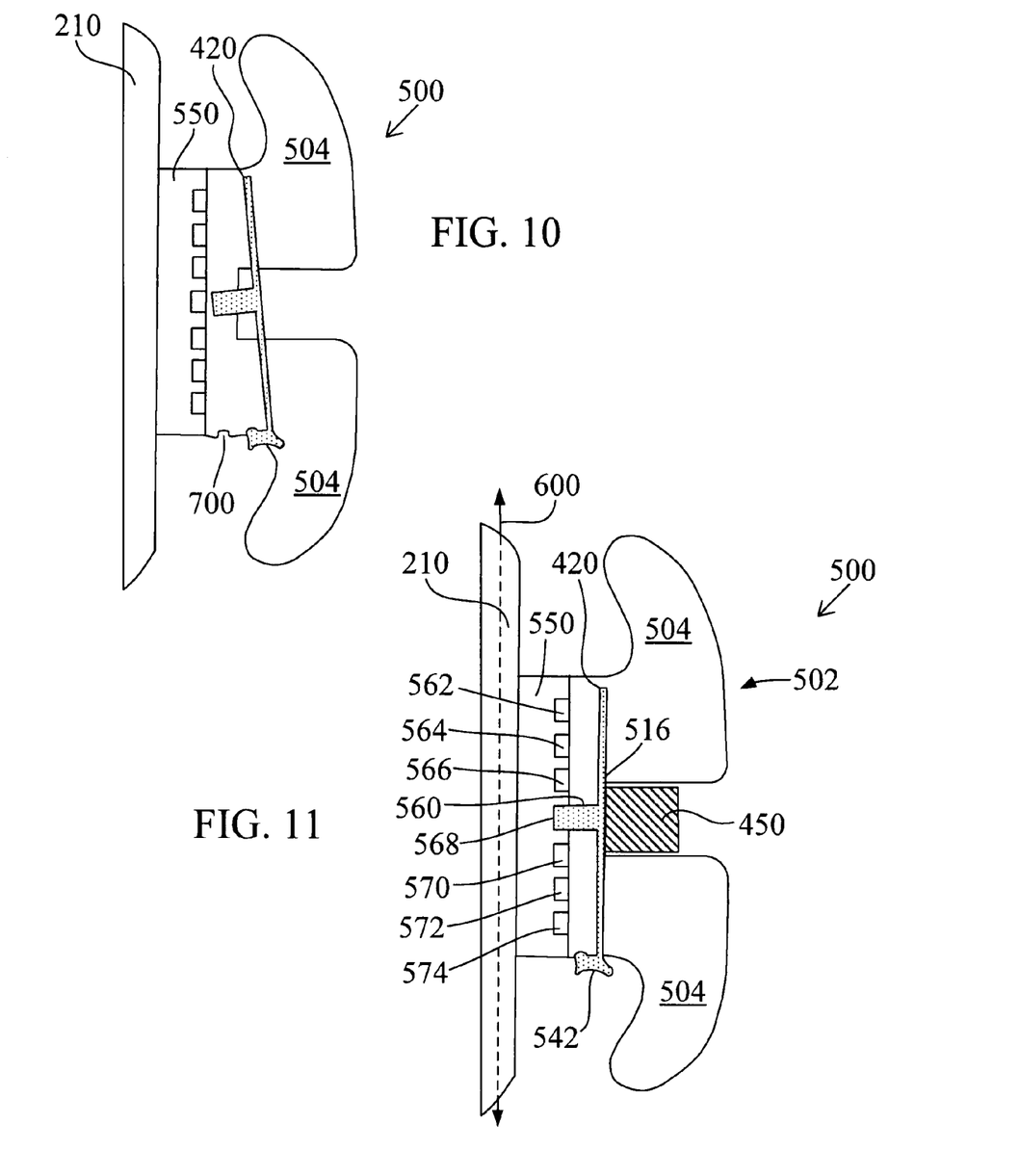
FIG. 10 is a partial side sectional view of a bracket which is made in accordance with the teachings of an alternate embodiment of the invention being selectively deployed upon a connector member which is made in accordance with the teachings of another alternate embodiment of the invention, before therapeutic wire is received.
FIG. 11 is a view which is similar to that which is shown in FIG. 10 but having therapeutic wire received it should be appreciated that the dark circles in FIGS. 1, 2, and 3 denote the use of a variable number of elements which respectively appear to the left and right of these respective circles.

Referring now to FIGS. 10 and 11, there is shown a bracket 500 which is made in accordance with the teachings of yet another alternate embodiment of the invention.

Particularly, bracket 500 has a front surface 502 which is substantially similar to front surface 402 (e.g., having four substantially similar protuberances 504 which are similar to each of the protuberances 406, 408, 410, 412. However, bracket 500 includes a member 516 which is pivotally coupled, like member 416 to the front surface 502 and which includes a member 542 which, like member 442, projects away from surface 502. However, unlike member 416, the member 516 additionally includes a projection 560 which projects away from the front surface 502. Further, unlike member 212, the member 550 includes equidistantly spaced slots, 562, 564, 568, 570, 572, and 574, each of which is adapted to selectively and frictionally and removably receive projection 560. In this manner, the position of the bracket 500 along axis 600 may be selectively modified (e.g., by selecting which slot 562-574 which is to received the projection 568, the position of the bracket 500 along axis 600 may be selected).

When it is desired to remove the bracket 500 from the member 210, the projection 560 is forcibly removed from whatever slot 566-574 it currently resides within, the member

542 is moved away from the detent 700, and the bracket 500 is slid off the member 210. Nothing in this description limits the invention to any particular number or types of slots 562, 564, 568, 570, 572, and 574 or to any particular number or type of members 560.

It is to be understood that the various inventions are not limited to the exact construction or methodology which has been delineated anywhere in this description, but that various changes and modifications may be made without departing from the spirit and the scope of the inventions as are delineated in the following claims.

What is claimed is:

1. An orthodontic connector assembly comprising a flat base portion having a flat tooth contacting adhering back surface and a flat front surface, said flat front surface further having a central protruding ridge which has a length less than the length of said flat front surface, and having a certain shape, and which is disposed along a longitudinal axis of said flat front surface, said central protruding ridge having a top edge;

said orthodontic connector assembly further comprising a bracket having a front portion with a wire reception slot and a back portion having a single slotted depression which has a shape which is complimentary to said certain shape of said central protruding ridge and wherein said single slotted depression having at least one ridge which is disposed within said single slotted depression and which extends along the width of said single slotted depression; and said central protruding ridge being selectively and movably disposed within said single slotted depression and wherein said top edge of said central protruding ridge engages said at least one ridge of said single slotted depression when said central protruding ridge is disposed within said single slotted depression, when said at least one ridge of said single slotted depression engages said top edge of said central protruding ridge, said central protruding ridge is secured within said single slotted depression, thereby coupling said first base portion to said bracket.

2. The orthodontic connector assembly of claim 1 wherein said certain shape of said central protruding ridge is a columnar shape.

3. The orthodontic connector assembly of claim 1 wherein said central protruding ridge is selectively movable within and along the length of said single slotted depression.

4. The orthodontic connector assembly of claim 3 wherein said certain shape of said central protruding ridge is a columnar shape.

* * * * *